United States Patent
Ryan et al.

(10) Patent No.: US 6,615,062 B2
(45) Date of Patent: Sep. 2, 2003

(54) REFERENCING OPTICAL CATHETERS

(75) Inventors: S. Eric Ryan, Hopkinton, MA (US);
Brett Bouma, Quincy, MA (US);
Guillermo J. Tearney, Cambridge, MA (US); Simon Furnish, Louisville, KY (US); Jing Tang, Allston, MA (US);
Andres Zuluaga, Boston, MA (US)

(73) Assignee: Infraredx, Inc., Cambridge, MA (US)

( * ) Notice: Subject to any disclaimer, the term of this patent is extended or adjusted under 35 U.S.C. 154(b) by 0 days.

(21) Appl. No.: 09/871,759

(22) Filed: May 31, 2001

(65) Prior Publication Data

US 2003/0097048 A1 May 22, 2003

(51) Int. Cl.$^7$ .................................................. A61B 5/00
(52) U.S. Cl. ...................... 600/310; 600/341; 356/243.1
(58) Field of Search ................................ 600/341, 473, 600/310, 322, 325, 327, 331, 332, 339; 356/448, 364, 369, 243.1

(56) References Cited

U.S. PATENT DOCUMENTS

| | | | |
|---|---|---|---|
| 4,050,450 A | * | 9/1977 | Polanyi et al. ............... 600/332 |
| 4,322,164 A | | 3/1982 | Shaw et al. .................. 356/243 |
| 4,650,327 A | | 3/1987 | Ogi ............................ 356/243 |
| 4,744,656 A | * | 5/1988 | Moran et al. ............ 356/243.1 |
| 4,904,085 A | * | 2/1990 | Spillman Jr. et al. ....... 356/364 |
| 5,305,744 A | * | 4/1994 | Pfeiffer et al. ........... 356/243.1 |
| 5,365,925 A | * | 11/1994 | Lee ........................ 356/243.1 |
| 5,455,177 A | | 10/1995 | Krause et al. ................. 436/8 |
| 5,939,610 A | | 8/1999 | Iwamoto et al. ............. 73/1.03 |

* cited by examiner

Primary Examiner—Eric F. Winakur
(74) Attorney, Agent, or Firm—Fish & Richardson P.C.

(57) ABSTRACT

The invention provides methods and apparatus to reference or normalize optical measurements, by removing or accounting for background factors and artifacts, such as motion artifacts, that arise during use of optical catheters.

32 Claims, 3 Drawing Sheets

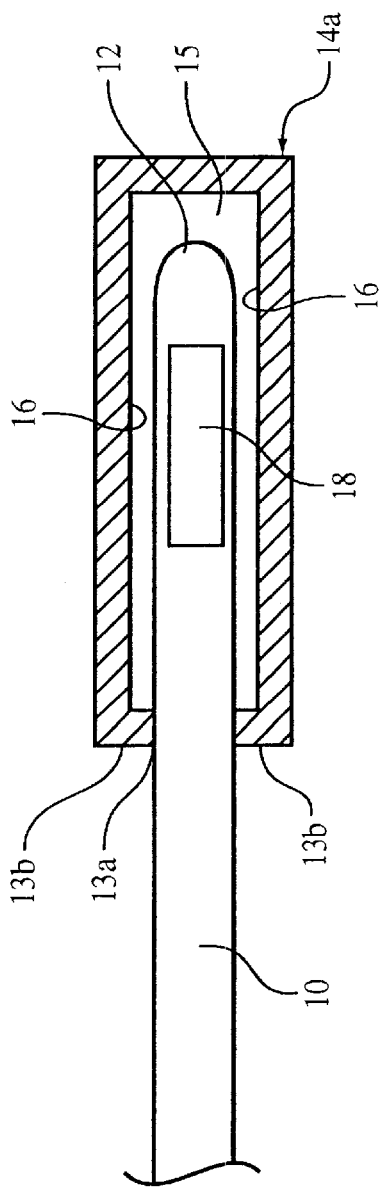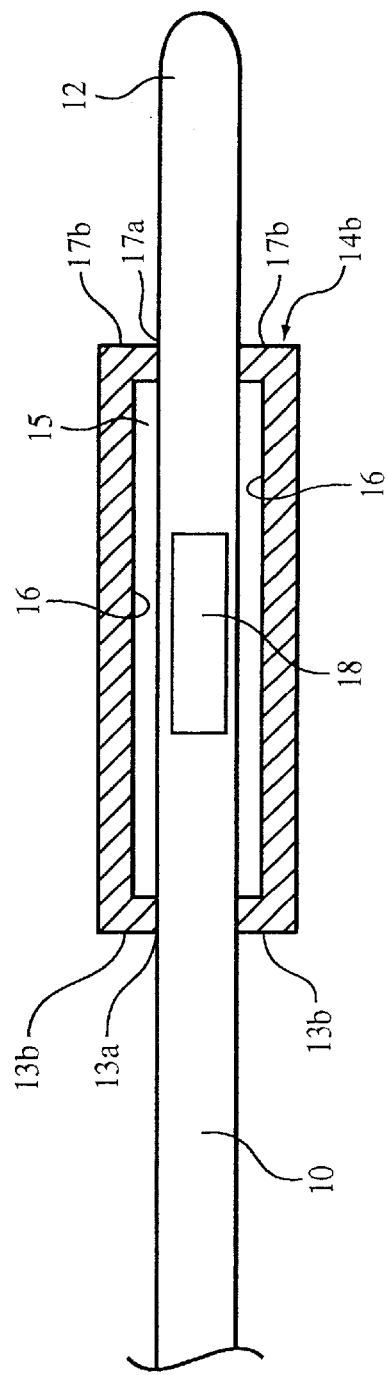

REFERENCING OPTICAL CATHETERS

TECHNICAL FIELD

This invention relates in vivo optical measurements, including but not limited to spectroscopy, incorporated in catheter-based implementations.

BACKGROUND

For intravascular optical measurements to be made reliably, various background factors and artifacts may need to be normalized or referenced. This includes factors and artifacts that exist or occur before and during the optical measurements.

Obtaining in vivo intravascular readings can be a difficult task. The environment is very harsh and not conducive to precise, reproducible optical measurements. First, the presence of blood, which is both highly scattering and absorbing, raises significant hurdles. The blood can vary in optically significant factors such as hematocrit (which varies scattering) and cholesterol content (which varies absorption), which can cause major variances in optical measurements from patient to patient.

Second, intravascular measurements can also be complicated by motion artifacts. This includes not only blood flow, but also cardiac motion in the case of coronary measurements. This motion can induce significant variances, for instance, in the output of a fiber delivery light to the distal end of catheter. These variances must be determined before accurate measurements can be made.

Finally, catheter technologies require complex, microscopic manufacturing processes that make it hard to provide exactly reproducible readings from catheter to catheter.

SUMMARY

The invention provides methods and apparatus to reference or normalize optical measurements, by removing or accounting for background factors and artifacts, such as motion artifacts. The invention provides methods for referencing factors due to equipment that can be addressed prior to use of an optical catheter, as well as factors due to the local measurement conditions in a patient that arise during use. Some of these factors are the same from patient to patient, such as the general nature of blood, and others vary from patient to patient, such as the specific constituents of each patient's blood.

In general, in one aspect the invention features an apparatus for calibrating an optical catheter. The apparatus includes a hollow well with a reflective internal surface; an entrance (and optionally an exit opening) arranged at a proximal end of the hollow well for inserting a catheter; and a sealing structure arranged in the entrance to contact the catheter during use to inhibit external light from entering the hollow well. The reflective internal surface can include a diffuse or direct reflective material. The apparatus can also include sealing structures arranged in the entrance and exit openings to contact the catheter during use to inhibit external light from entering the hollow well.

In another embodiment, the invention includes an apparatus for measuring back-reflection from the distal tip of an optical catheter that includes a beam sampler arranged to transmit a beam of electromagnetic radiation, e.g., visible light, from an electromagnetic radiation source, such as a laser, to the catheter and to receive and divert polarized electromagnetic radiation reflected from a proximal end of the catheter and unpolarized electromagnetic radiation back-reflected from the distal tip of the catheter; an optical redirector, e.g., a mirror or prism, arranged to direct polarized reflected electromagnetic radiation and unpolarized back-reflected electromagnetic radiation from the beam sampler to a polarizer; a polarizer arranged to selectively transmit unpolarized back-reflected electromagnetic radiation and block polarized reflected electromagnetic radiation; and a detector arrange to receive the unpolarized back-reflected electromagnetic radiation.

In another aspect, the invention features a method of generating a reference signal to normalize optical in vivo intravascular measurements for characteristics of a specific catheter by inserting a catheter into an environment comprising known optical characteristics; transmitting electromagnetic radiation through the catheter into the known environment; receiving and transmitting through the catheter any electromagnetic radiation reflected from the known environment; and processing the reflected electromagnetic radiation transmitted through the catheter to generate a reference signal that is specific for characteristics of the catheter. The method can be conducted prior to and/or after a catheterization procedure.

In these methods, the known environment can be a new reflecting apparatus as described herein including a hollow well and a reflective internal surface. The known environment can also be a liquid having known optical characteristics, such as scatter and absorbance. For example, the liquid can include styrene divinyl/benzene cross-linked copolymer beads suspended in an ultrapure aqueous solution. The new methods can be conducted when or after the catheter is manufactured, and the reference signal can be transcribed into computer-readable data or optically readable symbols.

In another aspect, the invention includes a method for normalizing optical in vivo intravascular measurements for variances in catheter output at the distal tip by transmitting electromagnetic radiation, e.g., light, from a source into the catheter; receiving electromagnetic radiation back-reflected from the distal tip of the catheter and transmitted through the catheter; processing the back-reflected electromagnetic radiation transmitted through the catheter to generate a reference signal specific for the back-reflected electromagnetic radiation; obtaining an actual in vivo intravascular measurement; and normalizing the actual measurement for variances in catheter electromagnetic radiation output at the distal tip by processing the actual measurement with the reference signal.

In one embodiment of this method, the electromagnetic radiation is polarized light, and the method further includes receiving polarized light reflected from a proximal end of the catheter; receiving unpolarized light back-reflected from the distal tip of the catheter; and removing the polarized reflected light from the unpolarized back-reflected light before processing the back-reflected light. The method can be conducted during a catheterization procedure, and processing can involve taking the ratio of the actual measurement over the reference signal, or subtracting the reference signal from the actual measurement.

The invention also features a method for normalizing an optical in vivo intravascular measurement in a patient by obtaining a catheter; illuminating a portion of the patient's blood with electromagnetic radiation emitted from the catheter; receiving electromagnetic radiation reflected from the blood; processing the reflected electromagnetic radiation to generate a reference signal that is specific for characteristics of the blood; taking an actual in vivo intravascular measurement in the patient; and normalizing the actual measurement by processing the actual measurement with the reference signal. In this method, the portion of the patient's blood can be in a blood vessel, wherein the method is conducted during a catheterization procedure. The portion of the patient's blood can also be in a container, wherein the method is conducted before and/or after a catheterization procedure. In these methods, the reference signal can be specific for, e.g., one or more of blood hematocrit and cholesterol.

In another aspect, the invention features a method for normalizing optical in vivo intravascular measurements in a patient by obtaining a catheter; illuminating a portion of vasculature in the patient with electromagnetic radiation emitted from the catheter; receiving electromagnetic radiation emitted from the portion of vasculature; processing the emitted electromagnetic radiation to generate a reference signal that is specific for characteristics of the portion of vasculature; taking an actual in vivo intravascular measurement in the patient; and normalizing the actual measurement by processing the actual measurement with the reference signal. In these methods, the portion of vasculature can be normal or diseased vasculature, e.g., vasculature that has a vascular disease other than lipid-rich, vulnerable atherosclerotic plaque, such as fibrous, stable atherosclerotic vasculature. These methods can be conducted before and/or after a catheterization procedure.

All of these new methods can be used individually or in combinations of any two or more methods. Similarly, the new apparatus can be used individually or in conjunction with each other. In addition, the invention features methods of obtaining reference measurements of the various components of the materials through which electromagnetic radiation travels from a catheter to the tissue, into the tissue, and back to the catheter to enhance the ability to discriminate measurements from the target.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 1A and 1B are schematic diagrams of catheters attached to a uniformly direct or diffuse reflecting apparatus.

DETAILED DESCRIPTION

Figure 2:
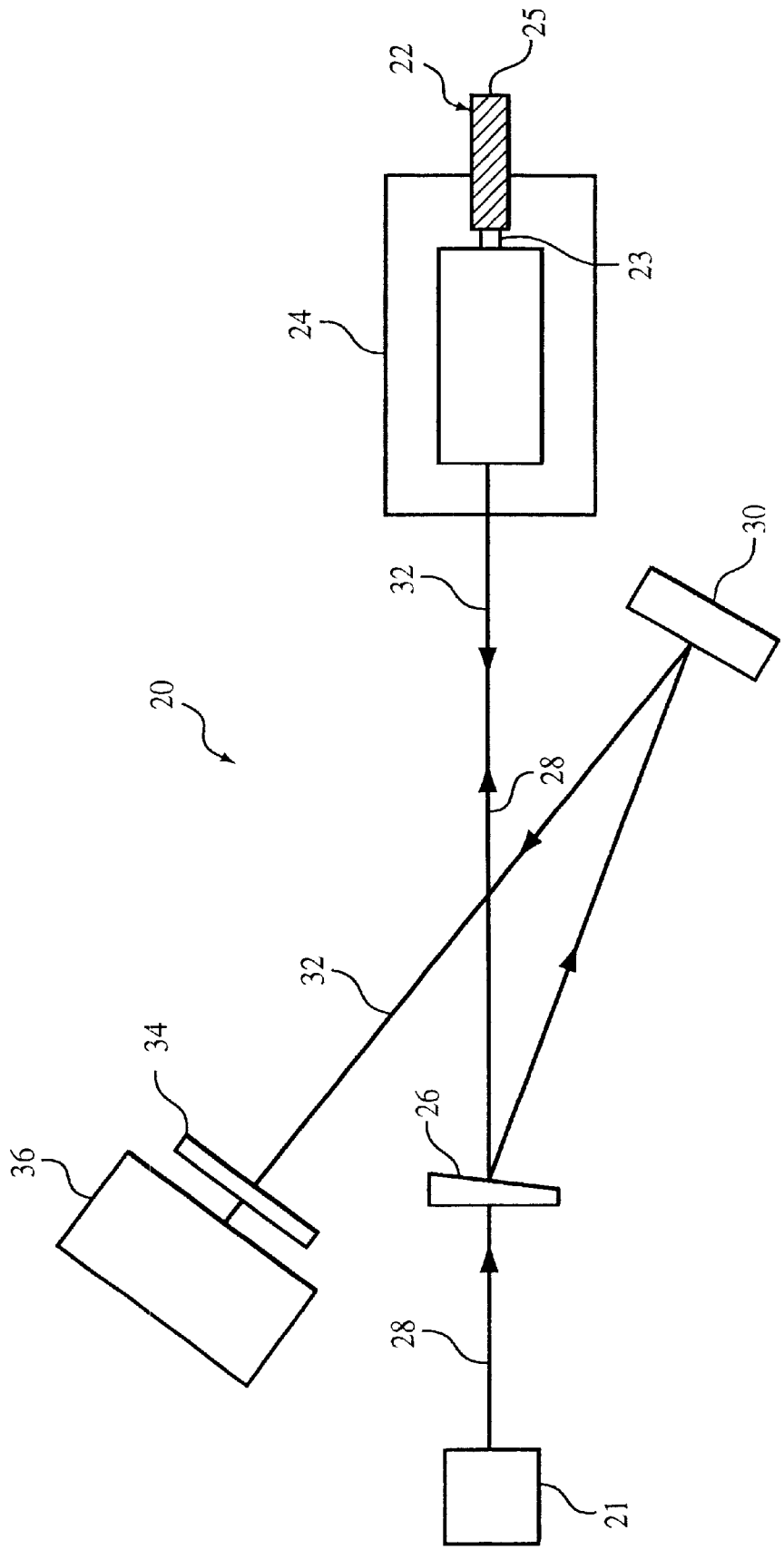
FIG. 2 is a schematic diagram of an optical system for collection of back-reflected light from the distal tip of a delivery catheter.

This invention is a collection of methods and devices that are designed to address optical referencing problems (factors such as artifacts, noise, and background) that arise during in vivo intravascular optical measurements. The methods include measurements made both before the catheterization procedure to reference catheter-specific factors, and measurements, e.g., made in real-time, during or before various catheterization procedures to reference patient-specific factors.

Referencing Catheter-specific Factors

Due to the complex manufacturing processes required for producing optical intravascular catheters, it is difficult to obtain perfectly repeatable results from catheter to catheter. Catheters can be normalized by taking a reference measurement of the catheter's characteristics before the catheterization procedure begins. This catheter-specific measurement is required to isolate the catheter's variances, because other optical system variances are often addressed during measurement procedures by methods such as optical beam sampling and measurement. These other calibrating methods usually focus on light source variances. Sequential reference measurements can be taken throughout the catheterization process to calibrate for electrical or detector variability, using standard techniques.

One method of taking such a reference measurement of catheter-specific variances is to place the catheter into an environment with known and constant optical characteristics. For example, the catheter, e.g., the tip or other portion of the catheter that includes an optical measurement area, can be inserted in to a reflection apparatus. FIG. 1A shows one such reflection apparatus 14a that is attached to the distal end 12 of a catheter 10 during manufacture or just prior to or just after a catheterization procedure. The benefit of having this apparatus attached during manufacture is that the entire combination, catheter and apparatus, can be sterilized and packaged at once. The benefit of using the apparatus after a catheterization procedure is that the operator no longer has to worry about maintaining sterility of the catheter.

Reflection apparatus 14a includes a hollow cylinder or end-capped well 15 that is internally coated with a reflecting layer 16 of a material such as gold or platinum that provides a high direct reflection. In other embodiments, materials that provide various degrees of diffuse reflection, such as brushed aluminum or Spectralon® (by Lab Spheres, Inc.), can be used as the reflecting layer 16. The material must be sufficiently thick such that effectively all of the light emitted by the catheter is reflected back into the catheter or is absorbed by the material. Tip apparatus 14a can be cylindrical or spherical to allow for uniform referencing, regardless of catheter orientation. The tip apparatus includes an entrance 13a to insert the catheter, but the apparatus should also allow minimal external light penetration. Thus, the apparatus should be made of a material that is opaque to the external light, such as an opaque plastic or metal, and have a relatively tight opening to insert the catheter. In addition, external light penetration can be minimized by placing an O-ring, flange, flap valve, or some other sealing structure 13b, made of a material that will not scratch the catheter, such as plastic, rubber, or silicone, at the entrance 13a of the tip apparatus 14. The tip apparatus must have sufficient depth such that no measurable reflected light comes from this sealing structure 13b back to the catheter tip.

As shown in FIG. 1B, another embodiment of this reflection apparatus 14b has both an entrance 13a and exit opening 17a with sealing structures 17b to accommodate catheters with long distal segments from the measurement point, e.g., catheters having features such as guide wires. In this embodiment, the optical measurement area 18 is not at the distal end 12 of catheter 10, but is set back from the end. In all embodiments, the important point is to insert the optical measurement area into the apparatus.

The reference reading can be taken before or after the catheterization procedure either by the optical system itself, or another specially-designed, dedicated optical device, which when connected to the catheter takes the optical measurements, and then the reflection apparatus can be removed. The reference reading can then be processed to generate a reference signal, e.g., an electrical signal, which is used by the optical system to normalize the actual sample readings measured using the tested catheter. Each catheter will have its own, unique reference reading/measurement and signal that the optical system takes into account when providing an output signal. The system can normalize the actual measurements for the catheter's unique characteristics by using standard chemometric methods including signal subtraction or taking the ratio of an actual measurement over the reference measurement.

Such chemometric techniques are described, for example, in Haaland and Thomas, "Partial Least Squares Methods for Spectral Analysis. 1. Relation to other Quantitative Calibration Methods and the Extraction of Qualitative Information," Analytical Chemistry, 60:1193–1202 (1988), and Stahle and Wold, "Multivariate Data Analysis and Experimental Design in Biomedical Research," in Progress in Medicinal Chemistry, Volume 25 (Ellis G P et al. (Eds.), Elsevier Science, 1988).

In other methods, the catheter can be placed into a permanent, non-disposable fixture attached to the optical system. This fixture has characteristics similar to those of the reflection apparatus of FIGS. 1A and 1B described above. In other embodiments, the environment with known and constant optical characteristics can be a liquid medium with a defined and constant scatter and absorbance characteristics, or some combination of the two. In these embodiments, the catheter is merely inserted into the appropriate liquid in a container. The primary aspect for the liquid to be measured for such a referencing method is that it must be pure. There are large, commercially available sources (such as BioRad) for a variety of pure liquids. The reading must be made through a sufficient depth of liquid, determined by the liquid, such that effectively all reflected light is from the liquid and not from the walls of the container holding the liquid. In addition, the container must be opaque to the wavelengths utilized for the reference measurement and to external light.

An example of a liquid that can be used in the new method and that has both defined scattering and absorbance characteristics comprises styrene divinyl/benzene cross-linked copolymer beads suspended in an ultrapure aqueous solution. This liquid is defined by appharma Analytical Standards, Inc. as a Certified Reference Standard, and has the following characteristics: the beads are defined as having a mean diameter of 0.121 $\mu$m; a particle count per liter of $7.95 \times 10^{14}$; a standard deviation of 0.104; a size distribution of 0.02–0.203 $\mu$m, and a refractive index (0.121 micron)= 1.5562.

Either way, reference readings are taken and the results are used as described above. Reference measurements made within such a liquid medium will most often be made after the catheterization procedure to avoid the need to sterilize the medium.

In another method, a reference measurement is made using one of the new methods when the catheter is manufactured, and the reference signal is transcribed into symbols, e.g., optically readable symbols such as a series of numbers or a bar code, and is provided to the optical system operator along with the catheter, for example, written or printed on the catheter or catheter packaging, for entry into the system. The reference signal can also be stored on a computer-readable medium, such as a diskette or magnetic tape or chip, and attached to or sent along with the catheter. Such reference data could include measurements of the direct or diffusely reflected signal received from the catheter, from within the apparatus or liquid described above, with a defined optical power input or the spectral absorbance characteristics of the catheter including UV, visible, near-infrared, and/or infrared wavelengths.

Referencing Patient-Specific Factors

It is also important to normalize readings between different patients by taking reference readings of factors specific to each patient.

For example, in one method, the patient's blood is used as a reference before, during, and/or after the catheterization procedure. This technique ensures that variances in the blood characteristics from patient to patient do not interfere with the measurement of the target tissue or material, unless the blood itself contains the target. In this case, reference measurements are made to remove any signal corresponding to the optical characteristics that are not intended to be part of the target signal. One example of this would be to measure the blood's scattering characteristics for those situations in which diffuse absorbance of the blood is measured.

Methods to incorporate this reference reading include obtaining blood from the catheterization site, or elsewhere, and then placing it in an apparatus with characteristic and constant optical properties, including, but not limited to, high direct or diffusely reflecting material. A reference measurement can then be made of the patient's blood and incorporated into the optical system for normalizing across variances in patient-to-patient blood. It is important to measure the patient's blood optical characteristics because factors such as hematocrit can significantly alter optical scatter, and blood cholesterol content can change absorbance or reflectance spectra. Ex vivo reference measurement of the patient's blood provides more accurate measurements due to the absence of motion and the removal of the possibility of measuring a vascular wall instead of a sufficient depth of blood.

To obtain reliable, reproducible optical readings in the volatile and constantly moving environment inside the vasculature, it is also beneficial to obtain real-time reference readings from the tip of the catheter from within a blood vessel. Due to the continuous bending of the catheter and subsequent changing bending losses within the fibers, the internal fibers can alter their output over time. Increasing the numerical aperture or cladding-to-core ratio of the fiber can reduce this characteristic, but it is also be important to obtain real-time referencing readings to account for these alterations in the output signal.

One method to obtain such a reference reading is to measure the back-reflection of electromagnetic radiation, such as light, from the distal tip of the delivery fiber or fibers. Though it is conceivable that a referencing fiber could be placed within the catheter to measure the delivered light, this fiber will have its own, and most likely dissimilar, bending losses at any given time, and thus may not be practical. To avoid the need for an internal referencing fiber, the optical system is specifically designed to preferentially gather this back-reflected light from the delivery fiber. In addition, this system must separate the electromagnetic radiation (e.g., light) that is reflected from the proximal end of a delivery fiber or catheter, from the radiation (light) that is back-reflected from the distal tip of the optical fiber or catheter.

FIG. 2, shows a system for use in this method. System 20 includes a light source 21 that emits a delivery beam 28, which passes through beam sampler 26 on its way to fiber coupler 24 and into catheter 22. Light reflected from the proximal end 23 of catheter 22 is returned along path 32 to beam sampler 26. This reflected light is polarized, just like delivery beam 28, because it has not entered catheter 22. Light that enters the catheter is transmitted to the distal tip 25 and is reflected back from the inside of the tip of catheter 22, passes back through the catheter, through fiber coupler 24, and is directed as a back-reflected beam along path 32 to the beam sampler 26. This back-reflected light is unpolarized by its travel through the catheter.

Beam sampler 26 receives both the reflected light and the back-reflected light and diverts portions thereof to a polarizer 34 via an optical redirector 30, such as mirror or prism, to detector 36, such as a PbS, PbSe, or InGas photodetector. Polarizer 34 is adjusted to minimize, and thus remove, the polarized reflected light form the proximal end of the optical fiber/catheter from the unpolarized back-reflected light that has been reflected from the distal tip of the optical fiber/catheter. By measuring this back-reflected light, the system can normalize the measurement for variances in light output at the end of the catheter, given that the total measured loss will be twice that of the losses in one direction along the catheter at any given moment. The actual measurements are normalized using standard chemometric methods including signal subtraction or taking the ratio of the actual measurement over the reference measurement.

Such chemometric techniques are described, for example, in Haaland and Thomas, 1988, supra, and Stahle and Wold, 1988, supra.

Figure 3:
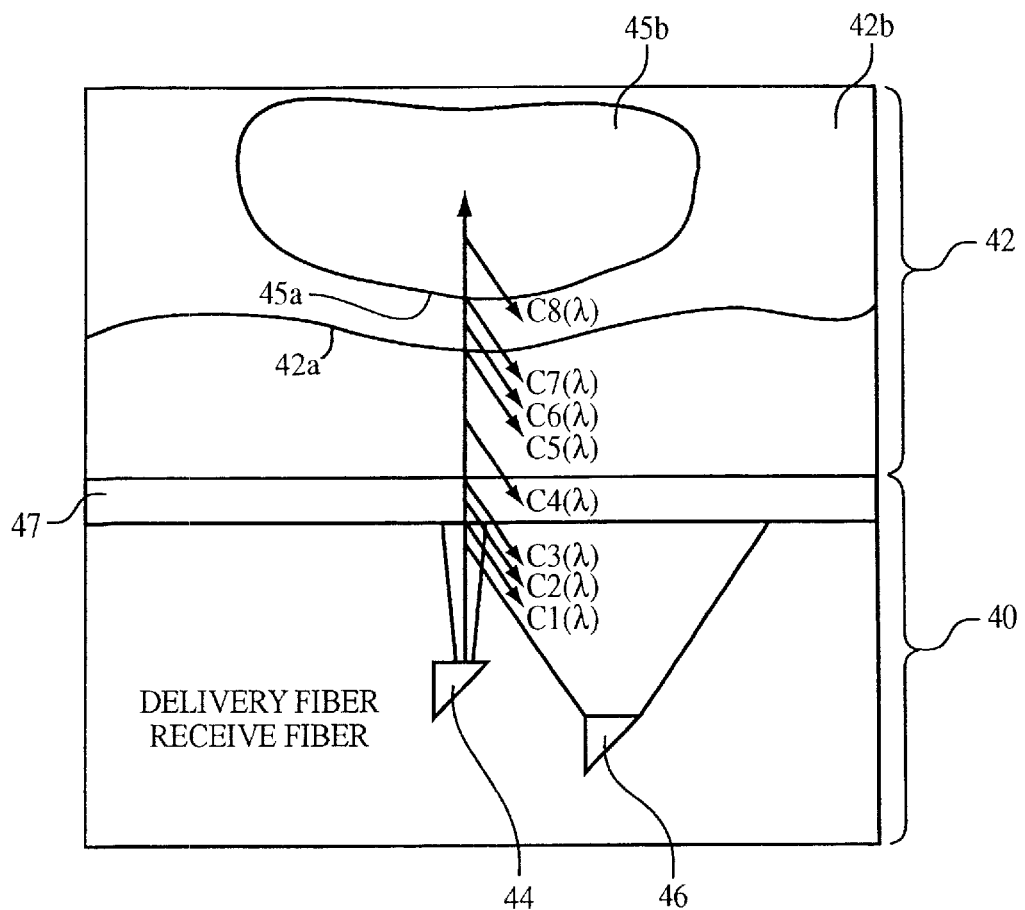
FIG. 3 is a schematic diagram of a catheter in a blood vessel showing the possible reference measurements that can be taken for each interface of different materials encountered in this environment.

It is also important to obtain reference measurements of the various components of the materials through which light travels from the catheter to the tissue, into the tissue, and back to the catheter to enhance the ability to discriminate any signal from the target. FIG. 3 schematically illustrates a catheter 40 with a delivery or output fiber 44 and an input fiber 46 and a transmission window 47, in blood 43 within a blood vessel 42. As light exists delivery fiber 44, it passes through the transmission window 47, the blood 43, the surface of the blood vessel wall 42a, the wall 42b itself, the surface of a lipid pool 45a, and into the lipid pool 45b, of a lipid-rich vulnerable atherosclerotic plaque. Each of these interfaces (e.g., device-element/device-element interface, device/sample interface or sample-component/sample-component interface within the sample) and materials can be measured for referencing. Thus, eight separate measurements can be made at the air or delivery fiber/transmission window interface $C1(\lambda)$, in the transmission window interior $C2(\lambda)$, the transmission/blood interface $C3(\lambda)$, the blood $C4(\lambda)$, the blood/vessel wall interface $C5(\lambda)$, the vessel wall interior $C6(\lambda)$, the vessel wall/lipid pool interface $C7(\lambda)$, and the lipid pool interior $C8(\lambda)$.

An example of such a measurement is to measure a large vessel, and thus obtain a measurement that is mostly contributed by blood, and then measure points in a smaller vessel, allowing for subtraction of the large vessel/blood measurement to better discriminate the contribution by the vessel wall in the subsequent readings.

Incorporation of a reference reading of the patient's blood during the catheterization procedure is another example of such a reference measurement. This method will reduce the requirement for external blood referencing measurements. In one example of this method, a physician takes a reference reading while in a large vessel, such as the aorta, to obtain a depth of blood sufficient to mimic an infinite depth for the optical measurement, which is between about 1 mm to 5 mm, depending primarily upon hematocrit levels and the wavelengths of light utilized. This procedure can be carried out using a self-centering and stabilizing mechanism such as a balloon. This reference measurement can be integrated into the optical system by using any of a variety of known referencing analysis methods described herein, including signal subtraction or taking the ratio of the actual measurement over the reference measurement.

Figure 4:
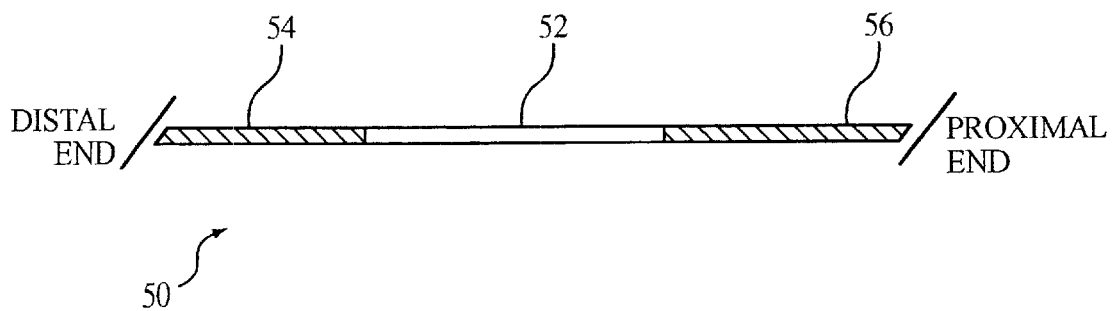
FIG. 4 is a schematic diagram of a guide catheter with an optically transparent transmission window.

An apparatus for use in the method described above can include a guide catheter 50 (shown schematically in FIG. 4), which is used to safely guide a catheter from the entry point of the body to the coronaries, and that is designed with a window 52 that is relatively optically transparent to the wavelengths to be utilized. Window 52 should be made of a well-defined material, such as different types of polyethylene, polyurethane, or Teflon®, with constant characteristics for incorporation into the referencing system. Such an apparatus will allow for relatively deep blood measurements, in the aorta for instance. The guide catheter 50 includes a distal end 54 and a proximal end 56. The window 52 is positioned between the proximal and distal ends so that the window 52 is within the aorta or vena cava when the guide catheter is fully in place.

Reference measurements can also be made of normal vasculature that would increase the selective capability for target identification. Such a method includes taking a measurement in a similarly sized, but normal, section of vasculature. The determination that a section can be designated "normal" by, e.g., visualization or additional measurements from other technologies such as coronary measurements utilizing intravascular ultrasound. This measurement could then be incorporated in the optical system to normalize the measurement by common analysis methods described herein and known to those skilled in this field to increase discrimination.

Similarly, reference measurements can also be made of diseased vasculature. In this case, a known atherosclerotic, stenotic lesion can be identified by fluoroscopy, or a catheter-based technology such as intravascular ultrasound and then imaged or illuminated to get a reference measurement. This would increase discrimination of characteristics such as lipid-pools within different stages of atherosclerotic diseased tissue. By measuring a particular disease state of each patient, such as fibrous, stenotic atherosclerosis, and the patient's unique optical features of that disease, common analysis methods such as partial least squares discriminate analysis will enable greater discrimination of variances in atherosclerosis outside of that disease state such as thin-capped fibroatheroma that contain lipid-pools.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An apparatus for calibrating an optical catheter, the apparatus comprising
   a receptacle having a reflective internal wall, and a reflective internal floor at a distal end thereof, the wall and the floor together defining a hollow well, the receptacle defining an entrance arranged at a proximal end thereof for receiving a catheter to be calibrated into the hollow well; and a sealing structure arranged in the entrance to contact the catheter during use to inhibit external light from entering the hollow well.

2. The apparatus of claim 1, wherein one of the reflective internal wall and the reflective internal floor comprises a diffuse reflective material.

3. The apparatus of claim 1, wherein one of the reflective internal wall and the reflective internal floor comprises a direct reflective material.

4. The apparatus of claim 1, wherein the internal wall defines a hollow well having a circular cross-section.

5. The apparatus of claim 1, wherein the reflective internal floor defines an exit opening.

6. The apparatus of claim 5, further comprising an additional sealing structure arranged in the exit opening to contact the catheter during use to inhibit external light from entering the hollow well.

7. An apparatus for measuring back-reflection from the distal tip of an optical catheter, the apparatus comprising
a beam sampler arranged to transmit a beam of electromagnetic radiation from an electromagnetic radiation source to the catheter and to receive and divert polarized electromagnetic radiation reflected from a proximal end of the catheter and unpolarized electromagnetic radiation back-reflected from the distal tip of the catheter;
an optical redirector arranged to direct polarized reflected electromagnetic radiation and unpolarized back-reflected electromagnetic radiation from the beam sampler to a polarizer;
a polarizer arranged to selectively transmit unpolarized back-reflected electromagnetic radiation and block polarized reflected electromagnetic radiation; and
a detector arranged to receive the unpolarized back-reflected electromagnetic radiation.

8. The apparatus of claim 7, wherein the optical redirector is a mirror.

9. The apparatus of claim 7, wherein the electromagnetic radiation is visible light.

10. The apparatus of claim 7, further comprising a fiber coupler for attaching the catheter to the apparatus.

11. A method for generating a reference signal to normalize optical in vivo intravascular measurements for characteristics of a specific catheter, the method comprising
inserting the specific catheter into a hollow well having a reflective internal wall and a reflective floor;
transmitting electromagnetic radiation through the catheter into the hollow well;
receiving and transmitting through the specific catheter any electromagnetic radiation reflected from the hollow well; and
processing the reflected electromagnetic radiation transmitted through the specific catheter to generate a reference signal that is specific for characteristics of the catheter.

12. The method of claim 11, further comprising performing a catheterization procedure after processing the reflected electromagnetic radiation.

13. The method of claim 12, wherein a reference signal specific for blood hematocrit is generated.

14. The method of claim 11, further comprising providing a receptacle defining the hollow well, the receptacle having
an entrance arranged at a proximal end of the hollow well for inserting the specific catheter; and
a sealing structure arranged in the entrance to contact the specific catheter during use to inhibit light from entering the hollow well; and
wherein inserting the specific catheter comprises inserting the specific catheter into the entrance of the receptacle.

15. The method of claim 11, further comprising providing a liquid having known scattering characteristics in the hollow well.

16. The method of claim 15, wherein providing the liquid comprises providing styrene divinyl/benzene cross-linked copolymer beads suspended in an ultrapure aqueous solution.

17. The method of claim 11, wherein the method is conducted after the specific catheter is manufactured, and the reference signal is transcribed into computer-readable data or optically readable symbols.

18. A method for normalizing optical in vivo intravascular measurements for variances in catheter output at the distal tip, the method comprising
transmitting electromagnetic radiation from a source into the catheter;
receiving electromagnetic radiation back-reflected from the distal tip of the catheter;
processing the back-reflected electromagnetic radiation to generate a reference signal specific for the back-reflected electromagnetic radiation;
obtaining an actual in vivo intravascular measurement; and
normalizing the actual measurement for variances in catheter electromagnetic radiation output at the distal tip by processing the actual measurement with the reference signal.

19. The method of claim 18, wherein the electromagnetic radiation is polarized light, and further comprising receiving polarized light reflected from a proximal end of the catheter; receiving unpolarized light back-reflected from the distal tip of the catheter; and removing the polarized reflected light from the unpolarized back-reflected light before processing the back-reflected light.

20. The method of claim 18, wherein the method is conducted during a catheterization procedure.

21. The method of claim 18, wherein processing involves taking the ratio of the actual measurement over the reference signal.

22. The method of claim 18, wherein processing involves subtracting the reference signal from the actual measurement.

23. A method for normalizing an optical in vivo intravascular measurement in a patient, the method comprising
obtaining a catheter;
illuminating a portion of the patient's blood with electromagnetic radiation emitted from the catheter;
receiving electromagnetic radiation reflected from the blood;
processing the reflected electromagnetic radiation to generate a reference signal that is specific for characteristics of the blood;
taking an actual in vivo intravascular measurement in the patient; and
normalizing the actual measurement by processing the actual measurement with the reference signal.

24. The method of claim 23, wherein the portion of the patient's blood is in a blood vessel, and the method is conducted during a catheterization procedure.

25. The method of claim 23, the portion of the patient's blood is in a container, and the method is conducted before a catheterization procedure.

26. The method of claim 23, wherein processing involves taking the ratio of the actual measurement over the reference signal.

27. The method of claim 23, wherein processing involves subtracting the reference signal from the actual measurement.

28. The method of claim 23, wherein a reference signal specific for blood cholesterol is generated.

29. A method for normalizing optical in vivo intravascular measurements in a patient, the method comprising obtaining a catheter;

illuminating a portion of vasculature in the patient with electromagnetic radiation emitted from the catheter;

receiving electromagnetic radiation emitted from the portion of vasculature;

processing the emitted electromagnetic radiation to generate a reference signal that is specific for characteristics of the portion of vasculature;

taking an actual in vivo intravascular measurement in the patient; and normalizing the actual measurement by processing the actual measurement with the reference signal.

30. The method of claim 29, wherein the portion of vasculature is normal vasculature.

31. The method of claim 29, wherein the portion of vasculature is diseased vasculature.

32. The method of claim 31, wherein the diseased vasculature comprises a disease other than lipid-rich, vulnerable atherosclerotic plaque.

* * * * *